(12) United States Patent
Murai et al.

(10) Patent No.: US 6,958,419 B2
(45) Date of Patent: Oct. 25, 2005

(54) ALKYNYL S,N-ACETAL DERIVATIVE AND METHOD OF PRODUCING THE SAME

(75) Inventors: Toshiaki Murai, Gifu (JP); Yuichiro Mutoh, Gifu (JP)

(73) Assignee: Gifu University, Gifu (JP)

( * ) Notice: Subject to any disclaimer, the term of this patent is extended or adjusted under 35 U.S.C. 154(b) by 0 days.

(21) Appl. No.: 10/734,850

(22) Filed: Dec. 11, 2003

(65) Prior Publication Data

US 2004/0167346 A1 Aug. 26, 2004

(30) Foreign Application Priority Data

Feb. 24, 2003 (JP) ......................................... 2003-046332

(51) Int. Cl.$^7$ ..................... C07C 323/27; C07C 323/29; C07C 209/68
(52) U.S. Cl. ........................ 564/501; 564/340; 564/423; 564/488
(58) Field of Search ................................ 564/340, 423, 564/488, 501; 556/423

(56) References Cited

FOREIGN PATENT DOCUMENTS

JP    2003-12613 A    1/2003

*Primary Examiner*—Brian Davis
(74) *Attorney, Agent, or Firm*—Crompton, Seager & Tufte, LLC

(57) ABSTRACT

An alkynyl S,N-acetal derivative of the present invention is represented by the following structural formula:

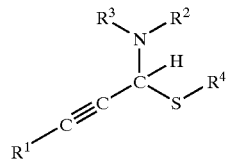

In the structural formula, $R^1$ represents a hydrogen atom, an alkyl group, an aryl group, an alkenyl group, a silyl group, or an alkynyl group; each of $R^2$ and $R^3$ represents an alkyl group or an allyl group; and $R^4$ represents an alkyl group. The alkynyl S,N-acetal derivative, which is a novel compound, is useful as a raw material of propargylamine.

10 Claims, No Drawings

ALKYNYL S,N-ACETAL DERIVATIVE AND METHOD OF PRODUCING THE SAME

BACKGROUND OF THE INVENTION

The present invention relates to alkynyl S,N-acetal derivatives used as, for example, a raw material of propargylamine, and a method of producing the same.

Propargylamine obtained by bonding a carbon atom to an alkynyl group and further bonding a hydrogen atom and a nitrogen atom to the carbon atom has physiological activity and, consequently, is utilized in chemical products and pharmaceuticals. Conventionally, propargylamine is synthesized from a propargylamine derivative obtained by bonding a carbon atom to an alkynyl group and further bonding an amino group and an alkyl group to the carbon atom. A propargylamine derivative is produced by reacting ammonia with a specific ester derivative such as 2-propynyl acetate, as disclosed, for example, in Japanese Laid-Open Patent Publication No. 2003-12613. However, reaction between an ester derivative and ammonia scarcely proceeds if a copper catalyst and a phase transfer catalyst such as tetramethylammonium bromide are not present.

SUMMARY OF THE INVENTION

Accordingly, it is an objective of the present invention to provide an alkynyl S,N-acetal derivative that is a novel compound useful as a raw material of propargylamine and a method of producing the same.

To achieve the foregoing and other objectives and in accordance with the purpose of the present invention, an alkynyl S,N-acetal derivative of the following structural formula is provided.

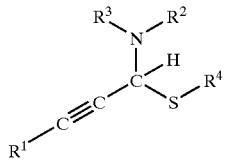

In the structural formula, $R^1$ represents a hydrogen atom, an alkyl group, an aryl group, an alkenyl group, a silyl group, or an alkynyl group; each of $R^2$ and $R^3$ represents an alkyl group or an allyl group; and $R^4$ represents an alkyl group.

The present invention also provides a method of producing an alkynyl S,N-acetal derivative of the following structural formula (1):

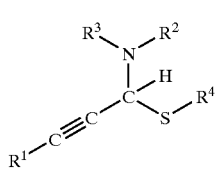

(1)

wherein $R^1$ represents a hydrogen atom, an alkyl group, an aryl group, an alkenyl group, a silyl group, or an alkynyl group; each of $R^2$ and $R^3$ represents an alkyl group or an allyl group; and $R^4$ represents an alkyl group. The method includes mixing thioformamide and an alkylating agent in a solvent to react the thioformamide and the alkylating agent, the thioformamide being represented by the following structural formula (2):

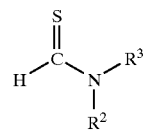

(2)

the alkylating agent containing a compound represented by the following structural formula (3):

$$R^4-X \quad (3)$$

and X representing a perfluoroalkylsulfonate; and further adding an alkynyl metal reacting agent into the solvent to react a reaction product of the thioformamide and the alkylating agent with the alkynyl metal reacting agent, the alkynyl metal reacting agent containing a compound represented by the following structural formula (4):

$$R^1-C\equiv C-M \quad (4)$$

and M representing an alkali metal atom.

Other aspects and advantages of the invention will become apparent from the following description, illustrating by way of example the principles of the invention.

DETAILED DESCRIPTION OF THE PREFERRED EMBODIMENTS

An embodiment of the present invention will be described below.

An alkynyl S,N-acetal derivative according to the present embodiment is a polyfunctional compound obtained by bonding a carbon atom to an alkynyl group and further bonding a sulfur atom, nitrogen atom and hydrogen atom to the carbon atom, and is represented by the following structural formula (1). In the structural formula (1), $R^1$ represents a hydrogen atom, an alkyl group, an aryl group, an alkenyl group, a silyl group, or an alkynyl group; each of $R^2$ and $R^3$ represents an alkyl group or an allyl group; and $R^4$ represents an alkyl group.

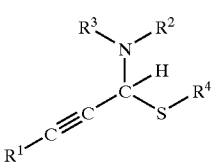

(1)

Specific examples of the alkyl group include a methyl group and a butyl group, specific examples of the aryl group include a phenyl group and a 4-chlorophenyl group, specific examples of the alkenyl group include a vinyl group and an allyl group, specific examples of the silyl group include a trimethylsilyl group, and specific examples of the alkynyl group include an ethynyl group and a propynyl group. Among them, alkynyl S,N-acetal derivatives in which $R^1$ represents an alkyl group, an aryl group, an alkenyl group, or a silyl group and each of $R^2$ to $R^4$ represents an alkyl group show high stability in air.

The alkynyl S,N-acetal derivative is synthesized by adding thioformamide and an alkylating agent to a solvent, and further adding an alkynyl metal reacting agent to this solvent.

The above-mentioned thioformamide is represented by the following structural formula (2). In the structural formula (2), each of $R^2$ and $R^3$ represents an alkyl group or an allyl group like $R^2$ and $R^3$ in the structural formula (1).

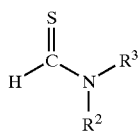 (2)

The above-mentioned alkylating agent contains a compound represented by the following structural formula (3). In the structural formula (3), $R^4$ represents an alkyl group like $R^4$ in the structural formula (1), and X represents a perfluoroalkylsulfonate.

$$R^4—X \quad (3)$$

The perfluoroalkylsulfonate is represented by the following structural formula (4). In the structural formula (4), n represents any integer of 1 to 8.

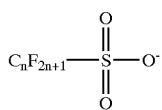 (4)

It is preferable that the perfluoroalkylsulfonate is triflate ion. The triflate ion is represented by the following structural formula (5):

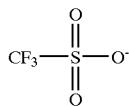 (5)

The above-mentioned alkynyl metal reacting agent contains a compound represented by the following structural formula (6). In the structural formula (6), $R^1$ represents a hydrogen atom, an alkyl group, an aryl group, an alkenyl group, a silyl group, or an alkynyl group like $R^1$ in the structural formula (1); and M represents an alkali metal atom. It is preferable that M represents a lithium atom.

$$R^1—C≡C—M \quad (6)$$

When an alkynyl metal reacting agent is further added to a solvent containing thioformamide and an alkylating agent, an alkynyl S,N-acetal derivative is formed together with an alkali metal salt of a perfluoroalkylsulfonate as a by-product, as indicated by the following reaction formula:

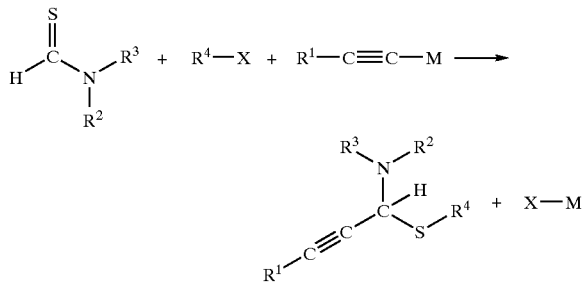

In the reaction of producing an alkynyl S,N-acetal derivative, thioformamide first reacts with a compound of the structural formula (3) to produce an intermediate, subsequently, the intermediate and a compound of the structural formula (6) react to produce an alkynyl S,N-acetal derivative.

It is preferable that the amounts of thioformamide, the compound of the structural formula (3), and the compound of the structural formula (6) are mutually chemical equivalents, namely, constituting a molar ratio of 1:1:1.

The solvent may be any solvent generally used in the field of synthetic organic chemistry. A preferable solvent is diethyl ether or tetrahydrofuran (THF). Diethyl ether or tetrahydrofuran does not particularly inhibit the reaction of producing an alkynyl S,N-acetal derivative.

In the reaction of producing an alkynyl S,N-acetal derivative, the reaction temperature is preferably from 0 to 30° C. and the reaction time is preferably from 15 to 60 minutes. When the reaction temperature is less than 0° C., the reaction speed may be slow to decrease the reaction efficiency, and when it exceeds 30° C., a solvent vaporizes depending on the kind of solvent. When the reaction time is less than 15 minutes, the yield may be lower, and when it exceeds 60 minutes, the reaction efficiency decreases.

The present embodiment has the following advantages.

The reaction of producing an alkynyl S,N-acetal derivative proceeds efficiently even if a catalyst is not used. In other words, an alkynyl S,N-acetal derivative is produced having good yield even if a catalyst is not used. The reason for this is deemed to be that each of thioformamide, a compound of the structural formula (3), and a compound of the structural formula (6) has high reactivity. The yield of an alkynyl S,N-acetal derivative is specifically from 50 to 80%, for example.

When X is a triflate ion, a compound of the structural formula (3) shows high reactivity with thioformamide.

When M represents a lithium atom, the compound of the structural formula (6) shows high reactivity with an intermediate of an alkynyl S,N-acetal derivative, namely, a reaction product of thioformamide and a compound of the structural formula (3).

An alkynyl S,N-acetal derivative is securely synthesized by adding thioformamide and an alkylating agent to a solvent, and further adding an alkynyl metal reaction agent to this solvent. When thioformamide and an alkynyl metal reaction agent are added to a solvent and then an alkylating agent is added to this solvent, thioformamide and a compound of the structural formula (3) do not react until an alkylating agent is added, and thereafter, its reaction product and a compound of the structural formula (6) react to produce an alkynyl S,N-acetal derivative. Therefore, the production efficiency of the alkynyl S,N-acetal derivative decreases. When an alkylating agent and an alkynyl metal reaction agent are added to a solvent and then thioformamide is added to this solvent, a compound of the structural formula (3) and a compound of the structural formula (6) react before addition of thioformamide. Therefore, a reaction product of thioformamide and a compound of the structural formula (3), namely, an intermediate of an alkynyl S,N-acetal derivative is scarcely produced.

It should be apparent to those skilled in the art that the present invention may be embodied in many other specific forms without departing from the spirit or scope of the invention. Particularly, it should be understood that the invention may be embodied in the following forms.

An alkynyl S,N-acetal derivative may be used not only as a raw material of propargylamine, but also as a raw material of compounds other than propargylamine, or may be used in applications other then raw materials. For example, an alkynyl S,N-acetal derivative may be used as a source of supplying a ligand of amines and the like, or may be used as a base compound for development of novel propargylamine.

An alkynyl S,N-acetal derivative may be synthesized by mixing a solvent containing thioformamide and an alkylating agent and a solvent containing an alkynyl metal reaction agent.

Next, the present invention will be further illustrated by examples and comparative examples.

EXAMPLE 1

Into a 20 mL volume two-necked flask dried under reduced pressure and purged with argon is charged 3 mL of diethyl ether, further, 0.1098 mL (1 mmol) of phenylacetylene and 0.625 mL (1 mmol) of n-butyllithium are added and the mixture is stirred at 0° C. for 15 minutes to prepare a first solution containing lithium acetylide. Next, into a 50 mL volume two-necked flask dried under reduced pressure and purged with argon are charged 3 mL of diethyl ether and 85.16 μL (1 mmol) of N,N-dimethylthioformamide, further, 113.2 μL (1 mmol) of methyl trifluoromethanesulfonate is added and the mixture is stirred at 20° C. for 30 seconds to prepare a second solution. To the second solution cooled to 0° C., the first solution is added through an L-shaped tube and the mixture is stirred at 20° C. for 30 minutes, and then filtrated. The filtrate is treated with saturated sodium hydrogencarbonate and anhydrous magnesium sulfate to remove unreacted substances and water contained in the filtrate, followed by further filtration and concentration. Then, 0.186 g of a dark red oily substance is obtained. The magnetic resonance spectrum of this substance is as described below when tetramethylsilane (TMS) is used as an internal standard and deutero-chloroform ($CDCl_3$) is used as a solvent.

$^1$H-NMR: δ2.29(s, 3H, SMe), 2.44(s, 6H, $NMe_2$), 4.91(s, 1H, CH), 7.26–7.34(m, 3H, Ar), 7.45–7.50(m, 2H, Ar). $^{13}$C-NMR: δ15.0(SMe), 40.8($NMe_2$), 64.5(CH), 84.0, 87.5 (C≡C), 122.5, 128.4, 131.8, 132.0(Ar).

The results suggest that the substance obtained in Example 1 is 3-dimethylamino-3-methylthio-1-phenyl-1-propyne of the following structural formula (7). In the structural formula (7), Ph represents a phenyl group and Me represents a methyl group.

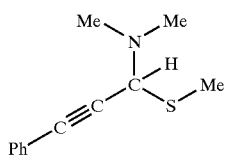

(7)

EXAMPLE 2

In Example 2, a first solution is prepared as described below. That is, in Example 2, into a 20 mL volume two-necked flask dried under reduced pressure and purged with argon is charged 3 mL of diethyl ether, and further 0.1475 mL (1 mmol) of 1-octyne and 0.625 mL (1 mmol) of n-butyllithium are added, and then the mixture is stirred at 0° C. for 15 minutes to prepare a first solution containing lithium acetylide. Otherwise, except as described above, Example 2 is carried out using the same procedure as in Example 1 to finally obtain 0.059 g of an orange oily substance. The magnetic resonance spectrum of this substance is as described below when tetramethylsilane is used as an internal standard and deutero-chloroform is used as a solvent.

$^1$H-NMR: δ0.89(t, J=6.9 Hz, 3H, $CH_3$), 1.29(sextet, J=12.7 Hz, 2H, $CH_2$), 1.40(quint, J=7.0 Hz, 2H), 1.53(quint, J=7.2 Hz, 2H, $CH_2$), 1.67(quint, J=7.4 Hz, 2H, $CH_2$), 2.21(s, 3H, SMe), 2.28(t, J=6.9 Hz, 2H, $CH_2$), 2.35(s, 6H, $NMe_2$), 4.68(s, 1H, CH). $^{13}$C-NMR: δ14.0($CH_3$), 14.9(SMe), 18.8 ($CH_2$), 22.5($CH_2$), 28.6($CH_2$), 28.7($CH_2$), 31.3($CH_2$), 40.6 ($NMe_2$), 64.4(CH), 74.9, 88.3(C≡C).

The results suggest that the substance obtained in Example 2 is 1-dimethylamino-1-methylthio-2-nonyne of the following structural formula (8). In the structural formula (8), n-$C_6H_{13}$ represents a normal hexyl group and Me represents a methyl group.

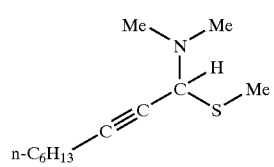

(8)

EXAMPLE 3

In Example 3, a first solution is prepared as described below. That is, in Example 3, into a 20 mL volume two-necked flask dried under reduced pressure and purged with argon is charged 3 mL of diethyl ether, and further 0.0951 mL (1 mmol) of 2-methyl-1-butyn-3-yne and 0.625 mL (1 mmol) of n-butyllithium are added. Then, the mixture is stirred at 0° C. for 15 minutes to prepare a first solution containing lithium acetylide. Otherwise, except as described above, Example 3 is carried out using the same procedure as in Example 1 to finally obtain 0.123 g of a dark-red oily substance. The magnetic resonance spectrum of this substance is as described below when tetramethylsilane is used as an internal standard and deutero-chloroform is used as a solvent.

$^1$H-NMR: δ1.91(s, 3H, $CH_3$), 2.29(s, 3H, SMe), 2.38(s, 6H, $NMe_2$), 4.8(s, 1H, CH), 5.25(s, 1H, $CH_2$), 5.33(s, 1H, $CH_2$). $^{13}$C-NMR: δ14.9(SMe), 23.5($CH_3$), 40.6($NMe_2$), 64.4(CH), 88.6, 83.0(C≡C), 122.3, 126.1(C≡C).

The results suggest that the substance obtained in Example 3 is 5-dimethylamino-5-methylthio-2-methyl-1-penten-3-yne of the following structural formula (9). In the structural formula (9), Me represents a methyl group.

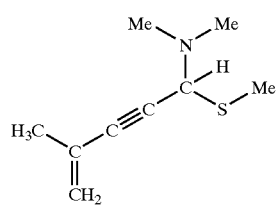

(9)

EXAMPLE 4

In Example 4, a first solution is prepared as described below. That is, in Example 4, into a 20 mL volume two-necked flask dried under reduced pressure and purged with argon is charged 3 mL of diethyl ether, and further 0.1366 mL (1 mmol) of p-chloro-phenylacetylene and 0.625 mL (1 mmol) of n-butyllithium are added. Then, the mixture is stirred at 0° C. for 15 minutes to prepare a first solution containing lithium acetylide. Otherwise, except as described above, Example 4 is carried out using the same procedure as in Example 1 to finally obtain 0.184 g of a red oily substance. The magnetic resonance spectrum of this substance is as described below when tetramethylsilane is used as an internal standard and deutero-chloroform is used as a solvent.

$^1$H-NMR: δ2.28(s, 3H, SMe), 2.43(s, 6H, NMe$_2$), 4.88(s, 1H, CH), 7.27–7.30(m, 2H, Ar), 7.37–7.42(m, 2H, Ar). $^{13}$C-NMR: δ15.0(SMe), 40.7(NMe$_2$), 64.5(CH), 85.1, 86.2 (C≡C), 120.9, 128.6, 133.1, 134.4(Ar).

The results suggest that the substance obtained in Example 4 is 3-dimethylamino-3-methylthio-1-p-chlorophenyl-1-propyne of the following structural formula (10). In the structural formula (10), Me represents a methyl group.

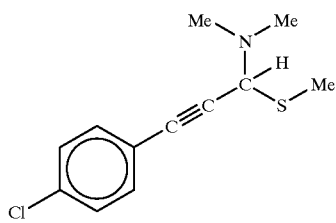

(10)

EXAMPLE 5

In Example 5, a first solution is prepared as described below. That is, in Example 5, into a 20 mL volume two-necked flask dried under reduced pressure and purged with argon is charged 3 mL of diethyl ether, and further 0.1017 mL (1 mmol) of trimethylsilylacetylene and 0.625 mL (1 mmol) of n-butyllithium are added. Then, the mixture is stirred at 0° C. for 15 minutes to prepare a first solution containing lithium acetylide. Otherwise, except as described above, Example 5 is carried out using the same procedure as in Example 1 to finally obtain 0.164 g of a red oily substance. The magnetic resonance spectrum of this substance is as described below when tetramethylsilane is used as an internal standard and deutero-chloroform is used as a solvent.

$^1$H-NMR: δ0.19(s, 9H, SiMe$_3$), 2.22(s, 3H, SMe), 2.35(s, 6H, NMe$_2$), 4.70(s, 1H, CH). $^{13}$C-NMR: δ0.1(SiMe$_3$), 14.9 (SMe), 40.6(NMe$_2$), 64.4(CH), 92.2, 99.5(C≡C).

The results suggest that the substance obtained in Example 5 is 3-dimethylamino-3-methylthio-1-trimethylsilyl-1-propyne of the following structural formula (11). In the structural formula (11), Me represents a methyl group.

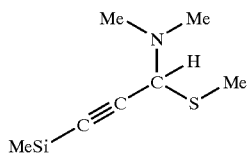

(11)

What is claimed is:

1. An alkynyl S,N-acetal derivative of the following structural formula:

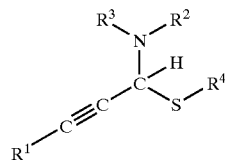

wherein R$^1$ represents a hydrogen atom, an alkyl group, an aryl group, an alkenyl group, a silyl group, or an alkynyl group; each of R$^2$ and R$^3$ represents an alkyl group or an allyl group; and R$^4$ represents an alkyl group.

2. The alkynyl S,N-acetal derivative according to claim 1, wherein R$^1$ represents an alkyl group, an aryl group, an alkenyl group, or a silyl group.

3. The alkynyl S,N-acetal derivative according to claim 1, wherein each of R$^2$ and R$^3$ represents an alkyl group.

4. The alkynyl S,N-acetal derivative according to claim 1, wherein R$^1$ represents an alkyl group, an aryl group, an alkenyl group, or a silyl group; and each of R$^2$ and R$^3$ represents an alkyl group.

5. A method of producing an alkynyl S,N-acetal derivative of the following structural formula (1):

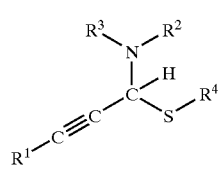

(1)

wherein R$^1$ represents a hydrogen atom, an alkyl group, an aryl group, an alkenyl group, a silyl group, or an alkynyl group; each of R$^2$ and R$^3$ represents an alkyl group or an allyl group; and R$^4$ represents an alkyl group, the method comprising:

reacting thioformamide and an alkylating agent in a solvent, the thioformamide being represented by the following structural formula (2):

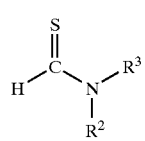

(2)

the alkylating agent containing a compound represented by the following structural formula (3):

(3)

and X representing a perfluoroalkylsulfonate; and
further reacting a reaction product of the thioformide and the alkylating agent with an alkynyl metal reacting agent in the solvent, the alkynyl metal reacting agent containing a compound represented by the following structural formula (4):

(4)

and M representing an alkali metal atom, where R$^1$, R$^2$, R$^3$, and R$^4$ are as previously defined with respect to structural formula (1).

6. The method according to claim 5, wherein X in the structural formula (3) represents a triflate ion.

7. The method according to claim 5, wherein M in the structural formula (4) represents a lithium atom.

8. The method according to claim 5, wherein the solvent is diethyl ether or tetrahydrofuran.

9. The method according to claim 5, wherein the reaction product of the thioformamide and the alkylating agent is reacted at a temperature of 0 to 30° C.

10. The method according to claim 5, wherein the reaction product of the thioformamide and the alkylating agent is reacted with the alkynyl metal reacting agent over a period of 15 to 60 minutes.

* * * * *

UNITED STATES PATENT AND TRADEMARK OFFICE
CERTIFICATE OF CORRECTION

PATENT NO. : 6,958,419 B2
DATED : October 25, 2005
INVENTOR(S) : Toshiaki Murai et al.

It is certified that error appears in the above-identified patent and that said Letters Patent is hereby corrected as shown below:

Column 7,
Line 60, delete structural formula 11 and insert:

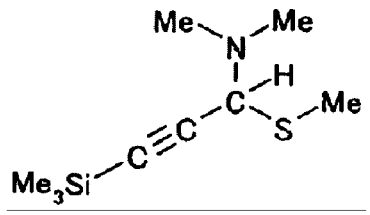

Signed and Sealed this

Seventh Day of February, 2006

JON W. DUDAS
*Director of the United States Patent and Trademark Office*